(12) United States Patent
Osterberg

(10) Patent No.: US 6,651,667 B2
(45) Date of Patent: Nov. 25, 2003

(54) MALE CONDOM

(76) Inventor: Brian J. Osterberg, P.O. Box 42, Petoskey, MI (US) 49770-0213

( * ) Notice: Subject to any disclaimer, the term of this patent is extended or adjusted under 35 U.S.C. 154(b) by 0 days.

(21) Appl. No.: 10/170,901

(22) Filed: Jun. 13, 2002

(65) Prior Publication Data
US 2002/0189619 A1 Dec. 19, 2002

Related U.S. Application Data
(60) Provisional application No. 60/297,848, filed on Jun. 13, 2001.

(51) Int. Cl.⁷ .................................................. A61F 6/04
(52) U.S. Cl. ........................................ 128/844; 128/918
(58) Field of Search ............................... 128/842, 844, 128/918; 604/347–353

(56) References Cited

U.S. PATENT DOCUMENTS

| | | | |
|---|---|---|---|
| 967,269 A | 8/1910 | Tibbs | |
| 4,846,197 A | * 7/1989 | Benjamin | 128/844 |
| 4,852,586 A | * 8/1989 | Haines | 128/842 |
| 4,919,149 A | * 4/1990 | Stang | 128/842 |
| 5,027,831 A | 7/1991 | Reddy | 128/844 |
| 5,082,004 A | 1/1992 | Reddy | 128/844 |
| 5,421,350 A | * 6/1995 | Friedman | 128/918 |
| 5,477,865 A | * 12/1995 | Broad | 128/842 |
| 5,486,322 A | 1/1996 | Fuchs | 264/46.5 |
| 5,823,191 A | 10/1998 | Cho | 128/844 |
| 5,836,307 A | 11/1998 | Scholl | 128/844 |
| 5,836,308 A | 11/1998 | Alla et al. | 128/844 |
| 6,000,398 A | 12/1999 | Alla et al. | 128/844 |
| 6,250,303 B1 | * 6/2001 | Delaney | 128/844 |

FOREIGN PATENT DOCUMENTS

| | | |
|---|---|---|
| DE | 6936640 | 7/1970 |
| DE | 42 25 160 C2 | 12/1992 |
| JP | 08033664 A | 2/1996 |
| JP | 10179626 A | 7/1998 |
| WO | WO 98/27898 | 7/1998 |
| WO | WO 01/097723 A1 | 6/2000 |
| WO | WO 00/62724 | 10/2000 |
| WO | WO 02/26174 A1 | 3/2001 |

* cited by examiner

*Primary Examiner*—Michael A. Brown
(74) *Attorney, Agent, or Firm*—Gifford, Krass, Groh, Sprinkle, Anderson & Citkowski, P.C.

(57) ABSTRACT

An improved male condom includes a flexible tubular body that is configured to cover a penis. The body includes a closed end and an open end. The closed end is configured to conform to a shape of the head of a penis. The open end is adapted to be positioned over the shaft of the penis. An inwardly projecting ridge is positioned on the closed end and extends along at least a portion of an inner circumference the tubular body. The ridge is configured to engage the rear of the penis head to thereby promote enhanced size, function and sensation for the user and his partner.

23 Claims, 2 Drawing Sheets

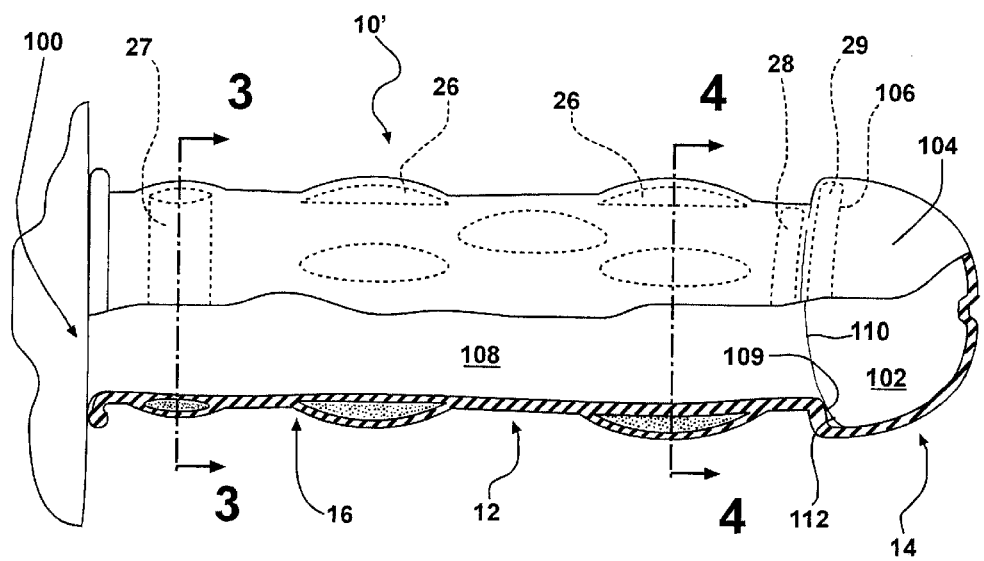
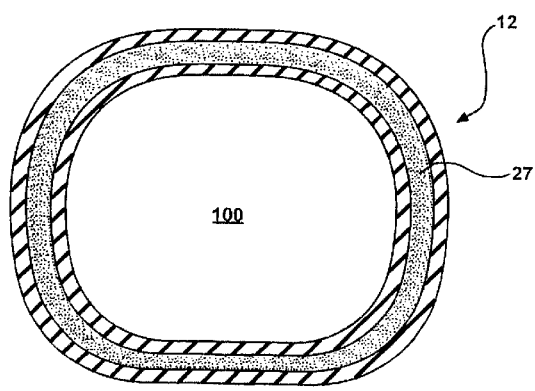
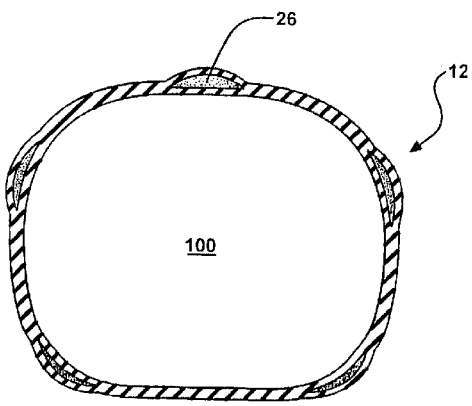

MALE CONDOM

RELATED APPLICATION

This application claims priority of U.S. Provisional Application Ser. No. 60/297,848 filed Jun. 13, 2001, which is incorporated herein by reference.

BACKGROUND OF THE INVENTION

1. Field of the Invention

This invention relates generally to prophylactic devices. More specifically, the invention relates to a condom for use by a male. Most specifically, the invention relates to a male condom having an anatomically correct shape.

2. Reference to Related Art

Condoms, when properly used, have been proven to prevent unwanted pregnancies and the communication of sexually transmitted diseases. Consequently, there are very strong incentives for their use. Condoms were originally manufactured from animal tissues. However, for reasons of health, safety and convenience, most condoms now in use are manufactured from elastomeric materials such as latex rubber, urethane polymers and the like.

Male condoms were initially economically, mass fabricated as simple, symmetrical tubular bodies of elastomeric material having a closed end and an open end. This massive scale of production allowed for very economical mass distribution to developing countries, as a form of financial and social assistance. Unfortunately, these condoms were configured to tightly fit against the penis and had very general, non-anatomical shapes, due to limitations in manufacturing latex-dipping techniques allowing only for economically mass-produced symmetrical-shaped condoms that could meet international standards for quality and safety and hence, widespread distribution in any country. While such condoms could effectively prevent disease and conception, it was found by many users that the condom's combination of shape and tight fit effectively bound and reshaped the penis thereby limiting sensation for both partners. Specifically, as the symmetrical, anatomically non-specific condom stretches tightly over the glans penis during coitus thrusting, the nonconforming latex eliminates the natural ridge-shape of a male coronal ridge and sulcus. The cause of this stretching is due to the fact that the condom is not formed, during manufacturing, to fit exactly to the ridges and protruding aspects of the glans penis as it is joined to the shaft of the penis. Consequently, with this problem affecting pleasurable sensations during coitus, couples often were reluctant to utilize condoms as a form of protection.

In an effort to overcome these problems, a second generation of male condoms was developed. The second-generation condoms are characterized by a very loose fit for the wearer at the closed end of the condom that allows the glans penis to better retain its natural shape by not having tight, clinging latex binding or stretching over the glans penis. These looser fitting condoms generally have symmetrical, widened closed ends or have non-symmetrical shapes near the closed end, such as protruding pouches or spirals. These "baggy" style condoms supposedly allow the wearer to be less subjected to changes in the coronal ridge shaping during use. Furthermore, the looser fit purportedly allow for the penis and vaginal tract to experience the frictional sensation associated with the loose latex creating folds in itself and creating friction between the partners' skin and the latex during coitus.

However, because of the excess loose latex, these condoms have been found to produce unnatural tactile sensations for some users and distracting noise during use. Additionally, the loose fit can cause problems with the user as the condom material can bunch up from all the folds created; or more detrimentally, unexpectedly slip off the penis during use. This potential for increased condom slippage is due to the looser fit and the increased friction between the latex folds created while in contact with the vaginal walls. The slippage would also interfere or eliminate pleasurable sensation, and of course, the pregnancy and disease protection being provided by the condom.

Manufacturing techniques have now progressed to the point where a form-fitting, anatomically correct, asymmetrical condom can now be mass-produced economically to meet the quality standards of all health organizations for distribution around the world (See e.g., U.S. Pat. No. 5,836,308.)

In addition to these traditional types of condoms, short or abbreviated condoms have been proposed that only cover a portion of a penis. For example, the contraceptive device of U.S. Pat. No. 3,648,700 discloses an abbreviated type condom that includes a receiver portion that is positioned over the glans penis and is secured to the penis by straps that wrap around the penis shaft. A radially outwardly extending bead is positioned at the rear of the receiver in an effort to mimic the natural form of a male penis.

The condom shown in U.S. Pat. No. 5,421,350 is only secured to the penis head. Specifically, an adhesive is applied on the interior of the condom to affix the condom to the penis head. Additionally, a flange lip is formed on the rear of the condom. The flange lip is integrally secured under the lip on the head of a penis and further assists the user in attaching the condom on the penis head.

Finally, U.S. Pat. No. 6,250,303 shows a male condom. The condom includes a bulb portion that fits over the head of a penis and a stiff, thick-walled belt that extends from the bulb portion and is securable around the shaft of the penis. The belt is stiff such that it cannot be rolled during use and so that it can prevent the passage of gas or fluids from the bulb. The front edge of the belt can be projected inwardly so that it provides a tight fit in the coronal sulcus and further prevents semen from passing back beyond the belt.

SUMMARY OF THE INVENTION

The present invention is directed to an improved male condom. The condom includes a flexible, sheath-like tubular body that is manufactured of elastomeric material. The body is configured to conformally cover a penis, has a closed end that conforms to the head of the penis (including the glans penis and corona) and an open end that is positioned over the penis shaft. An inwardly projecting ridge is positioned on the closed end, but can also be disposed on the body proximate the closed end. The ridge extends along a portion of an inner circumference of the tubular body and is configured to engage the rear of the head of the penis (including the coronal ridge and sulcus). A reservoir (or teat) for collected semen (and for ease of latex dip manufacturing processes) is positioned on the closed end of the body and, when manufactured, can project either inwardly or outwardly from the closed end.

In an alternative embodiment, the condom includes a body having a pocket. The pocket is filled with a filler material. Preferably, the filler material is a fluid (e.g., water, air or gel), but it can alternatively be a flexible material (e.g., a polymer). The pocket (or pockets) can be placed at any position along the body, but is preferably placed such that it is proximate the inwardly projecting ridge of the condom.

The condom of the present invention is anatomically configured so that it conforms and does not distort the penile shape and allows for the normal action and sensations caused by the male coronal ridge during sexual intercourse. This is accomplished by way of newly-developed manufacturing techniques in latex-dipping processes that will now allow for a mold created in the form of an actual male penis to be used for manufacturing a high-quality, safe, mass-produced condom. The biological and anthropological importance of the glans penis ridge is believed related to ease of entrance into the vaginal canal and to remove pre-existing semen from the canal as the penis is pulled back in a scraping motion out of the canal. Any improved manner in which the male penis can be left to, or retained to its closest original shape while wearing a condom is of utmost importance in creating promotion and awareness for greater condom usage in protection against AIDS, sexually transmitted diseases and pregnancy. Also, the psychological reasons for maintaining the actual shape of the glans penis while wearing an anatomically correct condom during sexual relations are myriad, as visual, physical and mental stimulation play large parts in providing incentives to wear condoms. The condom also affords the user the benefit of contraception and protection from disease, while preserving and in some instances enhancing the normal shape, function and sensation of the penis. As such, the condom does not interfere with function or sensation for either of the partners, and avoids the disincentives that have heretofore inhibited the responsible use of condoms.

BRIEF DESCRIPTION OF THE DRAWINGS

A clearer understanding of the present invention will be had upon reference to the appended figures wherein like reference numerals refer to like parts throughout and wherein:

FIG. 2 is a side cut-away view of condom constructed in accordance with an alternative embodiment of the present invention;

FIG. 3 is a sectional view taken along line 3—3 of FIG. 2; and

FIG. 4 is a sectional view taken along line 4—4 of FIG. 2.

DETAILED DESCRIPTION

Figure 1:
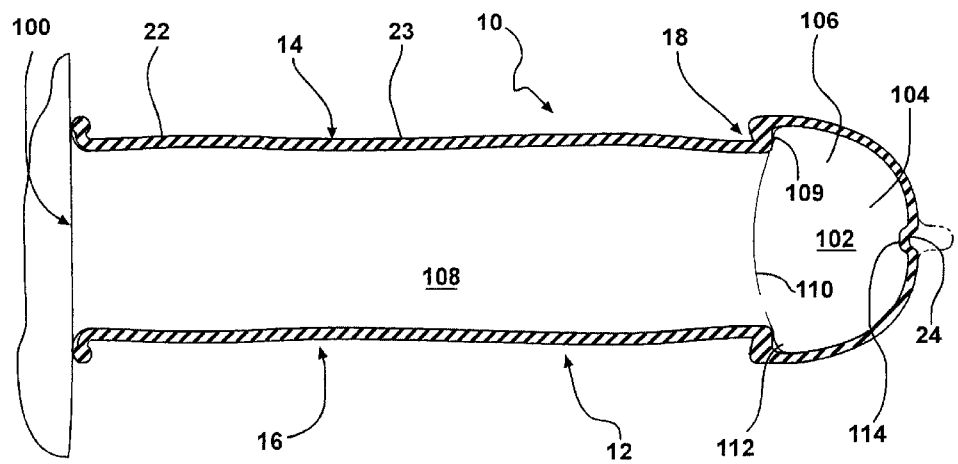
FIGS. 1 and 1A are side cut-away views of a condom constructed in accordance with a preferred embodiment of the present invention placed over a penis, and having a ridge oriented at an acute or obtuse angle.
Figure 1A:
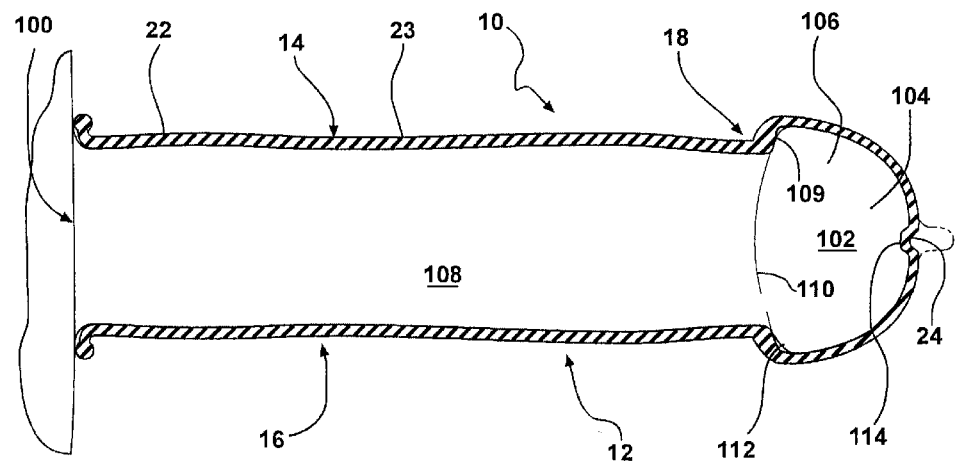

Referring now to FIG. 1, there is shown a preferred embodiment of an improved male condom 10 constructed in accordance with the present invention. The condom 10 includes a flexible, sheath-like tubular body 12 that is configured to cover a penis 100. The body 12 has a closed end 14 and an open end 16. The closed end 16 is configured to conform to the shape of the head 102 of a penis 100 (including the glans penis 104 and corona 106 of the head 102). The open end 16 is adapted to be positioned over the shaft 108 of the penis 100. An inwardly projecting ridge 18 is positioned relative to the closed end 14 and extends along at least a portion of an inner circumference 20 of the tubular body 12. Preferably, the ridge 18 is constructed to be integral with or otherwise incorporated onto the closed end 14. Alternatively, the ridge 18 can be disposed proximate the closed end 16. The ridge 18 is configured to engage the rear 109 of the penis head 102 (including the coronal ridge 110 and sulcus 112) to thereby preserve or promote enhanced size, function and sensation for the user and his partner.

Still referring to FIG. 1, the condom 10 can be manufactured by molding processes, or other techniques known in the art, which are presently used for condom manufacture. For example, the condom 10 can be manufactured using the methods shown in U.S. Pat. Nos. 5,836,308 and 6,000,398 to Alla et al., which patents and methods are incorporated herein by reference into this specification.

In order to provide the proper combination of anatomical correctness and fit, the condom 10 is preferably manufactured in several different sizes and widths. The material utilized for the manufacture of the condom 10 is preferably an elastomeric material. Therefore, it will be understood that a relatively small variety of sizes will suffice for most of the male population. More specifically, the tubular body 12 of the condom 10 is preferably manufactured of latex rubber. However, it will be appreciated that the condom 10 can also be manufactured from elastomeric materials such as urethane polymers, rubber, synthetic rubber or non-allergic plastic (e.g., surgical plastic). The thickness of a wall 22 of the body 12 is preferably uniform. Alternatively, the thickness of the wall 22 can be increased at the inwardly projecting ridge 18 (discussed below). As a still further alternative, the thickness of the wall 22 can be varied such that the outer surface 23 of the body 12 is texturized. Typical examples of texturized surface characteristics include the formation of ribs, dimples, dots or the like on the outer surface 23 of the body 12.

The open end 16 of the tubular body 12 is preferably a sheath of elastomeric material that is adapted to fit over the shaft 108 of the penis 100. As is known, the open end 16 can be packaged in a rolled form and subsequently unrolled over the penis shaft 108 prior to intercourse.

Still referring to FIG. 1, the closed end 14 of the body 12 is configured to fit over and conform to the shape of the penis head 102 (including the glans penis 104 and corona 106). An inwardly projecting ridge 18 is positioned relative to the closed end 14 and extends along at least a portion of an inner circumference 20 of the tubular body 12. Preferably, the ridge 18 is constructed to be integral with or otherwise incorporated onto the closed end 14. Alternatively, the ridge 18 can be disposed proximate the closed end 16. The ridge 18 is configured to engage the rear 19 of the penis head 102 (including the coronal ridge 110 and sulcus 112 of the penis 100) to thereby promote enhanced size, function and sensation for the user and his partner. The ridge 18 is preferably manufactured such that it forms a generally obtuse angle with respect to the open end (FIG. 1). However, the ridge 18 can also be formed at a right or acute angle to the open end.

As discussed above, the wall 22 of the body 12 including the ridge 18 has a uniform thickness. Alternatively, the ridge 18 can be formed by a buildup of latex on the inner circumference 20 of the body 20. However, regardless of the particular manufacturing method used, it will be appreciated that the engagement of the ridge 18 with the rear 109 of the penis head 102 simulates the coronal ridge 110 of the penis 100 and thereby provides enhanced sensation to the male user of the condom 10. Additionally, the ridge 18 allows the condom 10, particularly the closed end 14, to be conformally retained onto the penis 100.

The ridge 18 of the closed end 14 of the body 12 provides for normal penile action during intercourse; and in this regard, it allows for easier penetration, as well as for a natural stimulating action for the user's partner. Additionally, it has been theorized that the coronal ridge 110 of the penis 100 serves, among other things, to remove fluids, including previously deposited semen, from the vagina during intercourse. This cleaning function is retained when the condom 10 of the present invention is employed.

Still referring to FIG. 1, a reservoir 24 is provide at the closed end 14 of the condom 10 proximate the urinary meatus 114 to allow for collection and retention of ejaculate. The reservoir 24 is molded into the condom 10 such that it projects inwardly into the closed end 14 when in an unfilled state. This normally inwardly projecting reservoir 24 preserves the anatomically correct shape of the penis 100 and also prevents the penis 100 from sliding into the reservoir 24 during sexual intercourse; thereby compromising the fit and function of the condom 10.

Referring now to FIGS. 2–4 there is shown an improved condom 10' constructed in accordance with an alternative embodiment of the present invention. As with the preferred embodiment, the condom 10' can be manufactured by molding processes, or other techniques known in the art, which are presently used for condom manufacture.

As discussed above, the condom 10' of the alternative embodiment includes a flexible tubular body 12 that is configured to cover a penis 100. The body 12 has a closed end 14 and an open end 16. The closed end 16 is configured to conform to the shape of the head 102 of a penis 100 (including the glans penis 104 and corona 106 of the head 102). The open end is adapted to be positioned over the shaft 108 of the penis. An inwardly projecting ridge 18 is positioned relative to the closed end 14 and extends along at least a portion of an inner circumference 20 of the tubular body 12. Preferably, the ridge 18 is constructed to be integral with or otherwise incorporated onto the closed end 14. Alternatively, the ridge 18 can be disposed proximate the closed end 16. The ridge 18 is configured to engage a coronal ridge 110 and sulcus 112 of the penis head 102 to thereby promote enhanced size, function and sensation for the user and his partner.

Additionally, the condom 10' includes one or more pockets 26 that are filled with a filler material. A preferred filler material is a fluid such as air, water, gel or the like. Alternatively, the filler material can be a flexible material (e.g., a polymer). As best shown in FIG. 2, the pockets 26 serve to enhance the shape and/or size of the user's penis. The pockets 26 can be placed at any position along the body 12 and (as shown in FIGS. 2 and 3) can extend around the circumference of the body 14 (see e.g., pocket 27). However, it is preferred that at least one pocket 27 be positioned along the open end 16 of the body 12 to provide an enhancing effect to the shaft of the penis of the user. It is still more preferred that at least one pocket 29 be positioned so as to enhance the definition of the coronal ridge 110. It will therefore be appreciated that other pocket 28 placements may be employed for the condom 10'. Also, a greater or lesser number of pockets 26 than is shown in FIG. 2 may be utilized. Furthermore, while FIGS. 2–4 demonstrate that the pockets 26 are disposed on an anatomically correct condom 10', the pockets 26 can also be utilized in connection with condoms of other designs, including those of prior art configurations.

The foregoing drawings, discussion and description are illustrative of particular embodiments of the present invention, but are not meant to be limitations upon the practice thereof. In view of the foregoing, yet other modifications and variations of the present invention will be apparent to one of skill in the art. It is the following claims, including all equivalents, which define the scope of the invention.

I claim:

1. An improved male condom comprising:
   a flexible tubular body configured to conformally cover a penis having an outer surface, a closed end that is positionable over a head of said penis and an open end that is positionable over a shaft of said penis; and
   an inwardly projecting ridge on said closed end, said ridge having an acute angle with respect to outer surface of said body and being configured to engage a rear of said head of said penis.

2. The condom of claim 1, wherein said closed end is configured to conform to a shape of said head of said penis.

3. The condom of claim 1, further comprising a reservoir disposed on said closed end.

4. The condom of claim 3, wherein said reservoir is configured to project inwardly into said closed end when said reservoir is empty.

5. The condom of claim 1, further comprising a pocket positioned on said body.

6. The condom of claim 5, wherein said pocket is disposed proximate said inwardly projecting ridge.

7. The condom of claim 5, wherein said pocket is filled with a filler material.

8. The condom of claim 7, wherein said filler material comprises a fluid.

9. The condom of claim 8, wherein said fluid is selected from a group consisting of water, gel and air.

10. The condom of claim 7, wherein said filler material comprises a flexible material.

11. The condom of claim 10, wherein said flexible material comprises a polymer.

12. The condom of claim 1, wherein said body further comprises a texturized outer surface.

13. The condom of claim 1, wherein said body comprises a body wall having a uniform thickness.

14. The condom of claim 1, wherein said body comprises a body wall, said body wall having an increased thickness at said inwardly projecting ridge.

15. The condom of claim 1, wherein a thickness of a wall of said tubular body is greater at said projecting ridge.

16. An improved male condom comprising:
    a flexible tubular body configured to conformally cover a penis having a closed end, an open end and defining a pocket, said closed end being positionable over a head of said penis, said open end being positionable over a shaft of said penis and said pocket being filled with a flexible polymer filler material; and
    an inwardly projecting ridge on said closed end, said ridge extending along a portion of an inner circumference of said tubular body and being configured to engage a rear of said head of said penis.

17. The condom of claim 16, wherein said inwardly projecting ridge is formed at an obtuse angle with respect to said open end.

18. The condom of claim 16, wherein said inwardly projecting ridge is formed at an acute angle with respect to said open end.

19. The condom of claim 16, wherein said inwardly projecting ridge is formed at right angle with respect to said open end.

20. An improved male condom comprising:
    a flexible tubular body configured to conformally cover a penis having an outer surface, a closed end that is positionable over a head of said penis and an open end that is positionable over a shaft of said penis; and
    an inwardly projecting ridge on said closed end, said ridge having an obtuse angle with respect to the outer surface and being configured to engage a rear of said head of said penis.

21. The condom of claim 20, wherein said closed end is configured to conform to a shape of said head of said penis.

22. The condom of claim 20, further comprising a reservoir disposed on said closed end.

23. The condom of claim 22, wherein said reservoir is configured to project inwardly into said closed end when said reservoir is empty.

* * * * *